(12) United States Patent
Leathers et al.

(10) Patent No.: US 7,442,528 B2
(45) Date of Patent: Oct. 28, 2008

(54) MODIFIED ALTERNAN

(75) Inventors: Timothy D. Leathers, Peoria, IL (US); Melinda S. Nunnally, Washburn, IL (US); Gregory L. Cote, Edwards, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 341 days.

(21) Appl. No.: 11/387,313

(22) Filed: Mar. 23, 2006

(65) Prior Publication Data

US 2006/0166336 A1    Jul. 27, 2006

Related U.S. Application Data

(62) Division of application No. 10/235,132, filed on Sep. 5, 2002, now Pat. No. 7,049,105, which is a division of application No. 09/915,153, filed on Jul. 25, 2001, now Pat. No. 6,479,275.

(51) Int. Cl.
*C12P 19/04* (2006.01)
*C12N 1/14* (2006.01)
*C12N 1/16* (2006.01)

(52) U.S. Cl. .................. 435/101; 435/254.5; 435/256.3; 536/123.1; 536/123.2

(58) Field of Classification Search ........................ None
See application file for complete search history.

(56) References Cited

U.S. PATENT DOCUMENTS

| 5,702,942 | A | * | 12/1997 | Leathers et al. | ........... 435/252.9 |
| 5,786,196 | A | * | 7/1998 | Cote et al. | ................... 435/208 |
| 5,789,209 | A | * | 8/1998 | Leathers et al. | ............. 435/101 |
| 6,479,275 | B1 | * | 11/2002 | Leathers et al. | .......... 435/256.3 |
| 7,049,105 | B2 | * | 5/2006 | Leathers et al. | ............. 435/101 |
| 2005/0059633 | A1 | * | 3/2005 | Van Geel-Schuten | ........ 514/54 |

\* cited by examiner

*Primary Examiner*—Herbert J. Lilling
(74) *Attorney, Agent, or Firm*—John Fado; Randall E. Deck; Lesley Shaw

(57) ABSTRACT

Four new *Penicillium* spp. isolates (NRRL 21966, NRRL 21967, NRRL 21968, and NRRL 21969) are capable of essentially quantitative conversion of native alternan to a polymeric modified form having a lower apparent molecular weight than native alternan. A fifth isolate (NRRL 30489) obtained from a survey of deposited organisms and classified as a *Penicillium subgenus Biverticillium* has the same ability. The modified alternan has rheological properties similar to ultrasonicated alternan and is produced without the expense of ultrasonication. It would have utility as a substitute for gum arabic for uses such as bulking agents and extenders in foods and cosmetics.

4 Claims, 16 Drawing Sheets

MODIFIED ALTERNAN

CROSS REFERENCE TO RELATED APPLICATIONS

This application is a DIV of U.S. Pat. No. 10/235,132 09/05/2002 7,049,105, which is a DIV of U.S. Pat. No. 09/915,153 07/25/2001 now U.S. Pat. No. 6,479,275.

BACKGROUND OF THE INVENTION

1. Field of the Invention

This invention relates to a modified alternan having a lower apparent molecular weight than native alternan and to a method for producing the modified alternan. The modified alternan is produced by cultivation of native alternan in the presence of a *Penicillium* sp. isolate capable of essentially quantitative conversion of the native alternan to a polymeric modified form. The rheological properties of the modified alternan are similar to commercial gum Arabic.

2. Description of the Prior Art

The polysaccharide alternan was first described by Jeanes et al. (1954, *J. Am. Chem. Soc.*, 76:5041-5052) as one of two extracellular α-D glucans, referred to as fraction S, produced by *Leuconostoc mesenteries* NRRL B-1355. The structure of this fraction was later determined by Misaki et al. (1980, Carbohydr. Res., 84:273-285) to consist primarily of an alternating sequence of α-1,3-linked and α-1,6-linked D-glucose residues, with approximately 10% branching. Because the α-1,3-linkages are part of the linear chain of the S fraction and there are not any consecutive α-1,6- linkages, the fraction is not a true dextrin, and Cote and Robyt (1982, Carbohydr. Res., 101:57-74) therefore named this fraction alternan. These authors also isolated the enzyme alternansucrase which synthesizes alternan from sucrose.

Native alternan has an apparent molecular weight average ($\overline{M}_w$) of $10^6$-$10^7$ [Cote G. L., (1992), Carbohydrate Polymers 19:249-252; Cote G. L. et al., (1997), Alternan and highly branched limit dextrans: Low-viscosity polysaccharides as potential new food ingredients. In: Spanier A. M. et al. (ed) Chemistry of Novel Foods, Carol Stream, IL.: Allured Publishing Corp, pgs. 95-110]. Derivatives of alternan have been produced by ultrasonication, reducing the apparent molecular weight average to <$10^6$ and modifying the rheological properties of the polymer so that they more closely resemble gum Arabic [Cote, 1992, Ibid]. However, ultrasonication is a relatively expensive process that would be difficult to carry out on an industrial scale. Although alternan is resistant to hydrolysis by most known endoglucanases, a "limit alternan" has also been produced by treatment of native alternan with isomaltodextranase from *Arthrobacter globiformis* [Cote, 1992, Ibid]. Limit alternan exhibited an apparent $\overline{M}_w$ of $3.5 \times 10^3$ and was rheologically similar to oligosaccharides of maltodextrin [Cote, 1992, Ibid]. Recently, *Bacillus* sp. isolates were described that produced an endoglucanase specific for alternan [Biely P. et al., (1994), Eur. J. Biochem., 226:633-639; Cote G. L. et al., (1998), U.S. Pat. No. 5,889,179; Wyckoff H. A. et al., (1996), Curr. Microbiol., 32:343-348]. This enzyme produced a novel cyclic tetrasaccharide from alternan [Cote G. L. et al., (1994), Eur. J. Biochem., 226:641-648].

The desire to further extend the range of properties of modified alternan and to expand the scope of new applications for these materials has led to a continued search for new organisms, particularly fungi, that could partially degrade or modify the native polysaccharide.

SUMMARY OF THE INVENTION

We have now discovered four new *Penicillium* spp. isolates capable of essentially quantitative conversion of the native alternan to a polymeric modified form (hereafter referred to as "modified alternan") having a lower apparent molecular weight than native alternan. The rheological properties of the modified alternan are similar to commercial gum Arabic. A fifth isolate having the same apparent ability to convert native alternan to a lower molecular weight form was found in a survey of isolates of *Penicillium subgenus Biverticillium* obtained from a culture collection.

In accordance with this discovery, it is an object of this invention to provide novel fungal organisms for reducing the apparent molecular weight of alternan.

Another object of this invention is to provide a method for reducing the apparent molecular weight of alternan by cultivating the native form of this polysaccharide with novel *Penicillium* spp. isolates.

It is also an object of the invention to provide a composition of modified alternan, composed of novel low molecular weight fractions and having functional properties similar to those of gum arabic.

A further object of the invention is to produce a polysaccharide product having properties similar to those of ultrasonicated alternan, but without the expense of ultrasonication.

Yet another object of the invention is to provide novel compositions for use as bulking agents and extenders in foods and cosmetics, especially as carbohydrate-based soluble food additives.

Other objects and advantages of this invention will become obvious from the ensuing description.

DEPOSIT OF BIOLOGICAL MATERIAL

Figure 1:
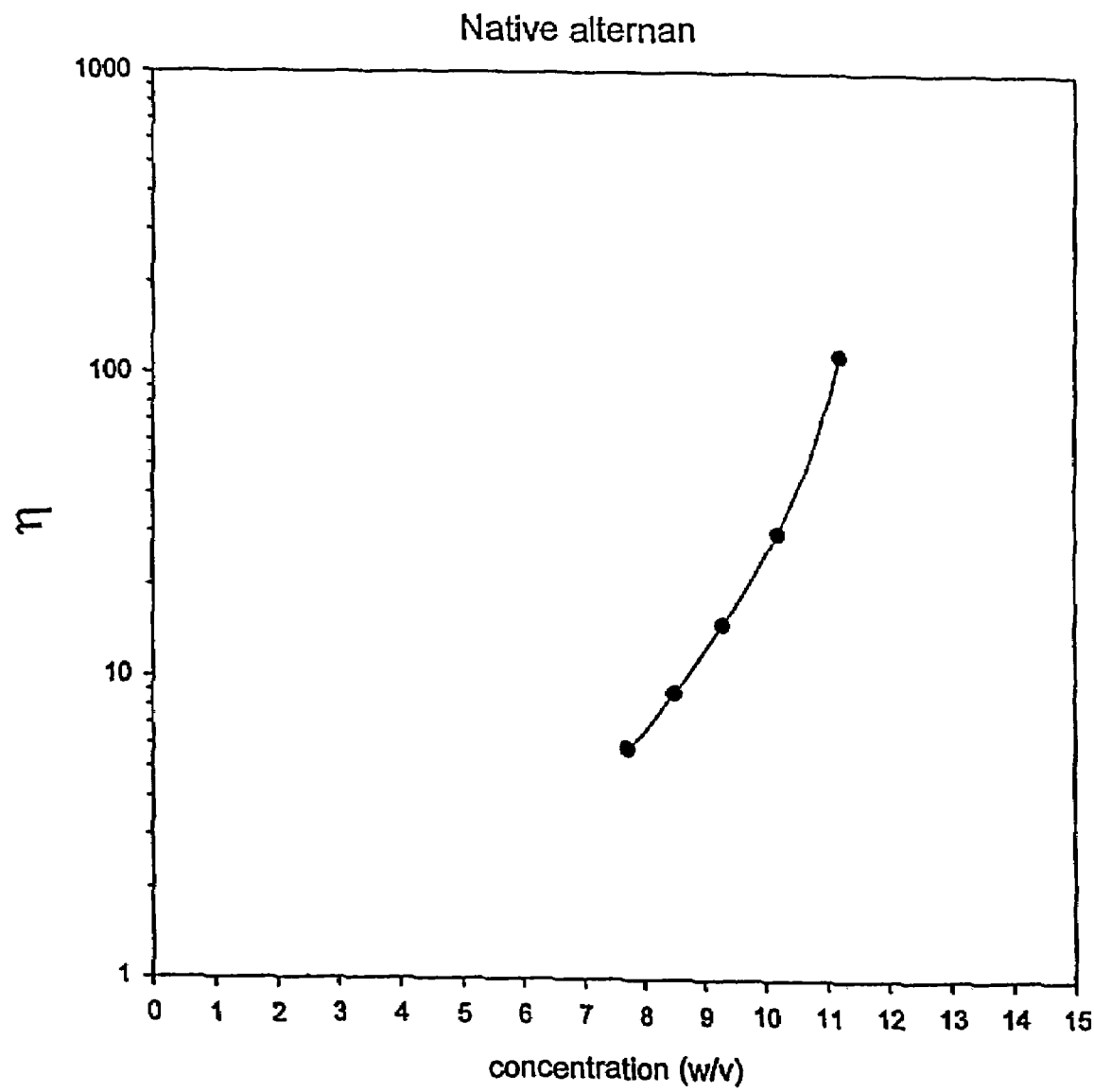
FIG. 1 is a plot of the relative viscosity (η) of native alternan as a function of concentration.
Figure 2:
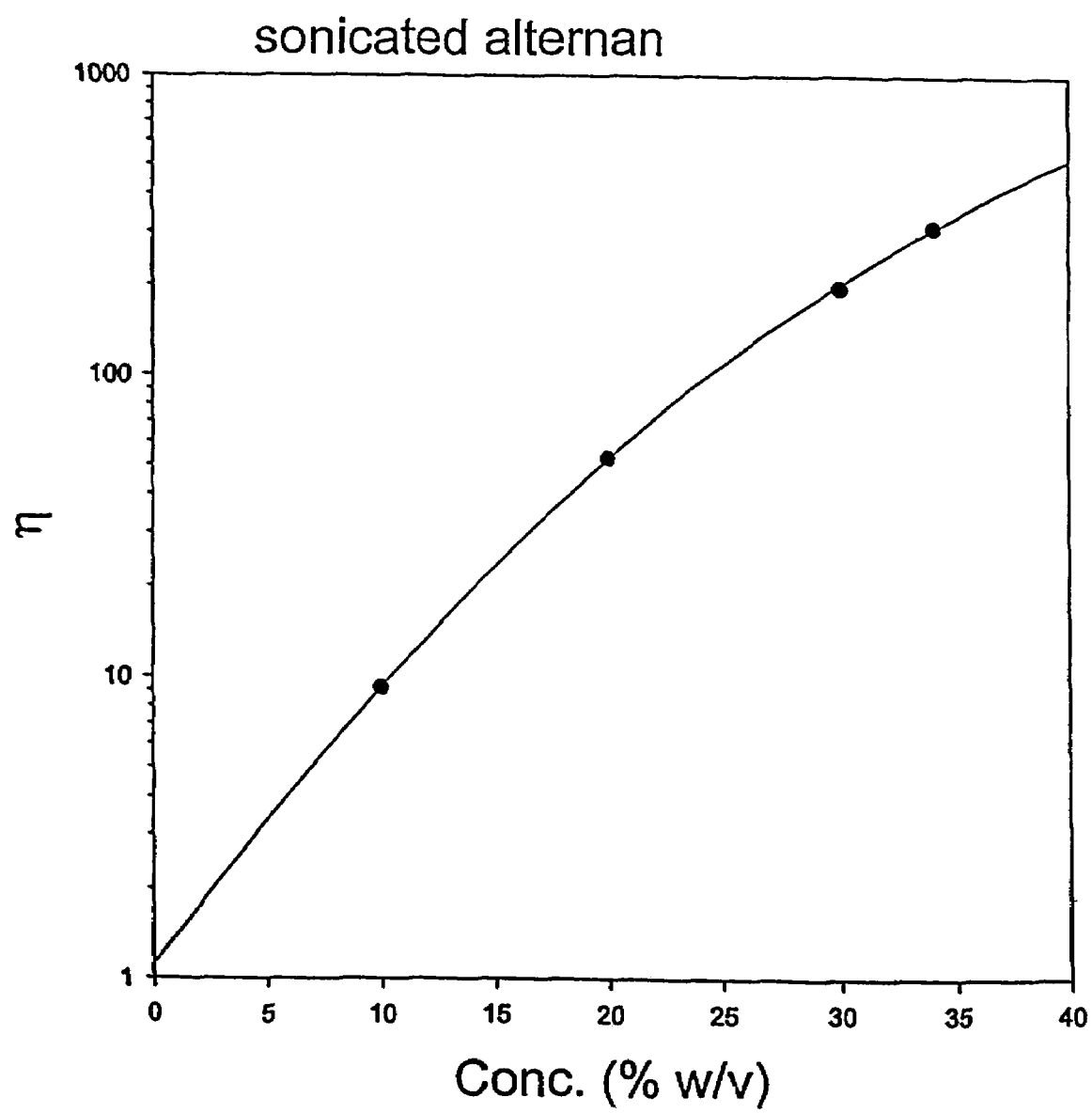
FIG. 2 is a plot of the relative viscosity (η) of sonicated alternan as a function of concentration.
Figure 3:
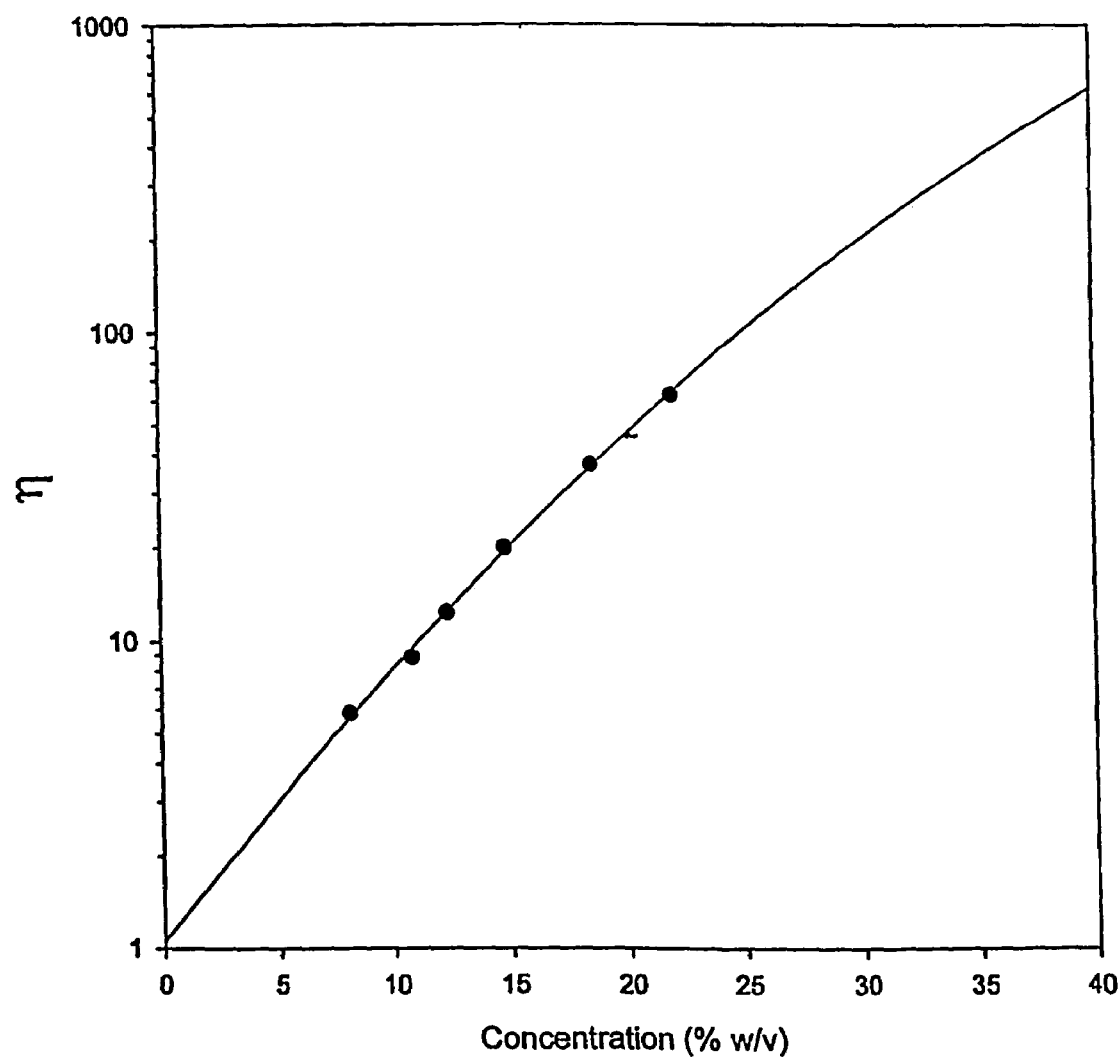
FIG. 3 is a plot of the relative viscosity (η) of modified alternan as a function of concentration.
Figure 4:
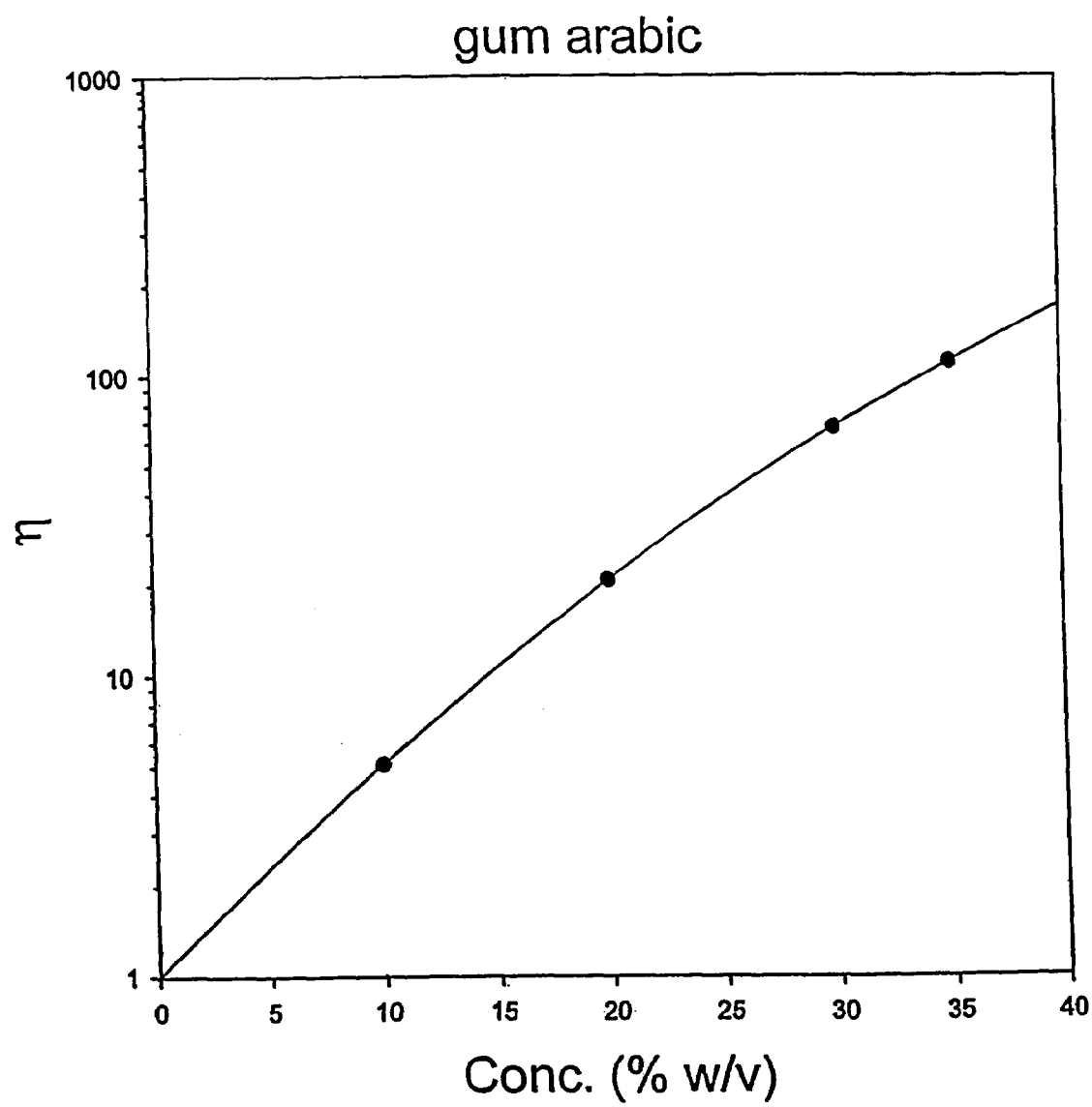
FIG. 4 is a plot of the relative viscosity (η) of gum arabic as a function of concentration.
Figure 5:
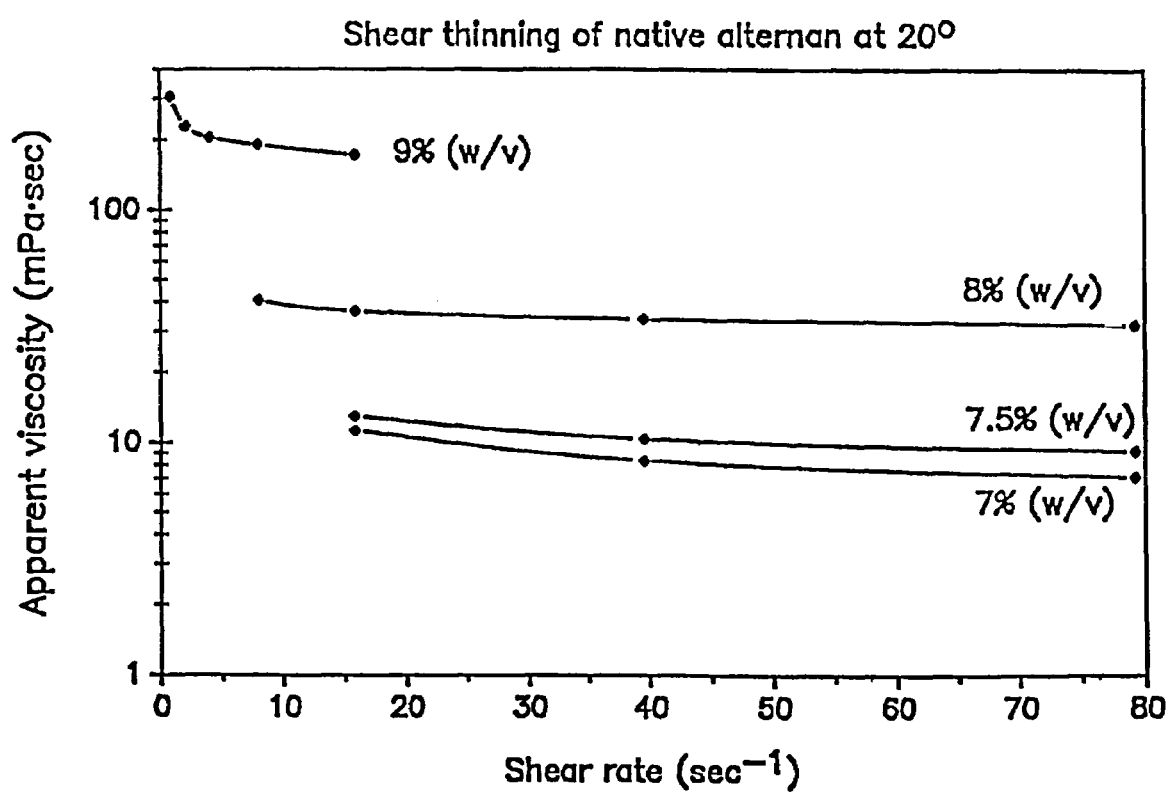
FIG. 5 is a plot illustrating the shear thinning properties of native alternan at various concentrations.
Figure 6:
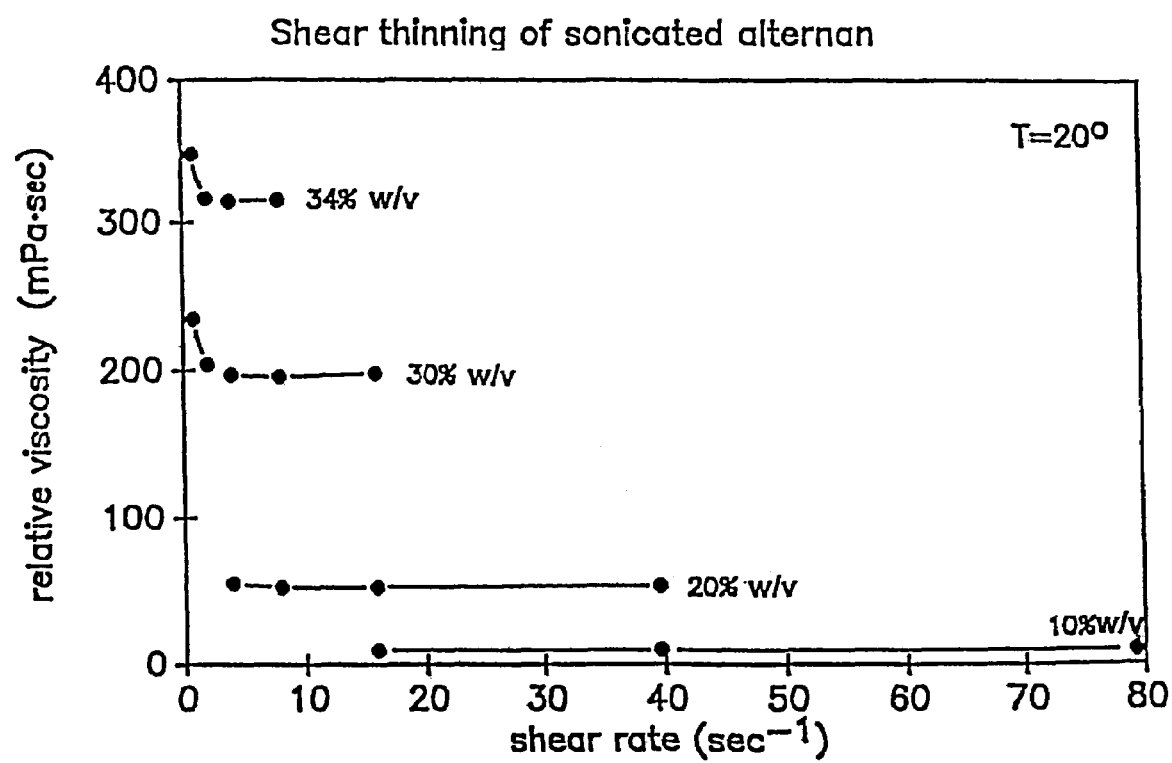
FIG. 6 is a plot illustrating the shear thinning properties of sonicated alternan at various concentrations.
Figure 7:
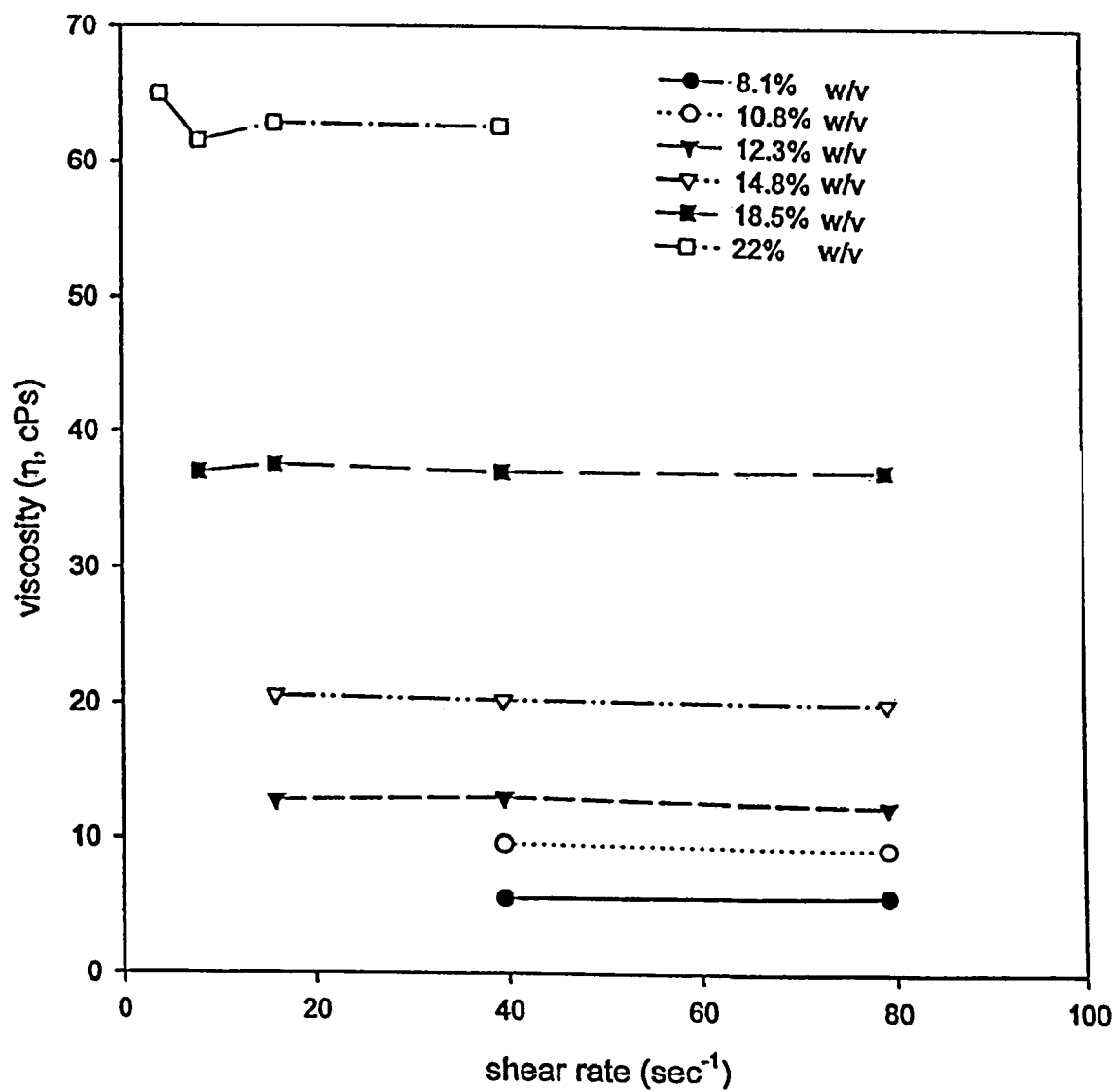
FIG. 7 is a plot illustrating the shear thinning properties of modified alternan at various concentrations.
Figure 8:
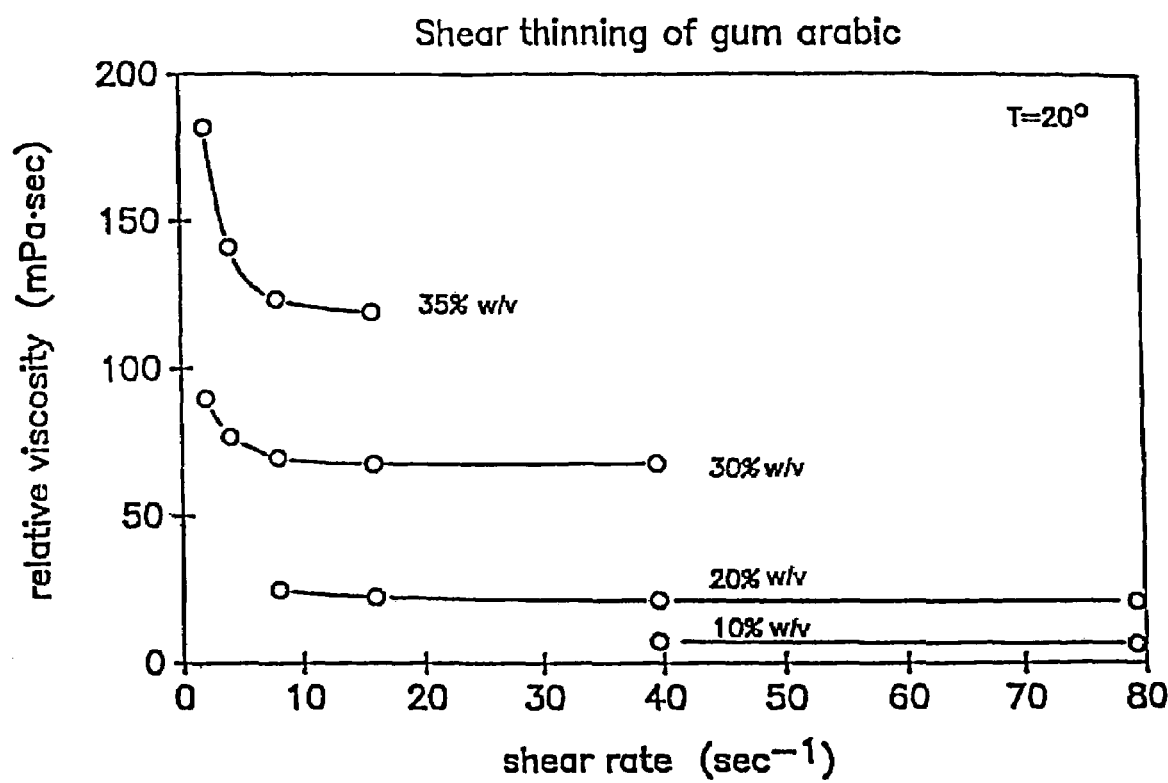
FIG. 8 is a plot illustrating the shear thinning properties of gum arabic at various concentrations.

Four *Penicillium* spp. isolates described further below were deposited on Mar. 26, 1998, under the provisions of the Budapest Treaty in the Agricultural Research Culture Collection (NRRL) in Peoria, IL, and have been assigned Accession Nos. NRRL 21966, NRRL 21967, NRRL 21968, and NRRL 21969. A fifth *Penicillium* spp. isolate was deposited on Jul. 20, 2001, under the provisions of the Budapest Treaty in the Agricultural Research Culture Collection (NRRL) in Peoria, IL., and has been assigned Accession No. NRRL 30489. All five of these isolates have the morphological characteristics of strains belonging to *Penicillium subgenus Biverticillium*.

DETAILED DESCRIPTION

The native alternan starting material for use in the invention may be prepared by conventional fermentation or enzymatic reaction. Suitable processes for producing alternan are known in the art and include, but are not limited to, fermentation with *Leuconostoc mesenteroides* NRRL B-1355, B-1498, or B-1501 as described by Jeanes et al. (1954, *J. Am. Chem. Soc.*, 76:5041-5052, the contents of which are incorporated by reference herein), or reaction of sucrose with alternansucrase as described by Cote and Robyt (1982, Carbohydr. Res., 101:57-74, the contents of which are incorporated by reference herein).

Production of the modified alternan of the invention is carried out by cultivation of the native alternan with one or more of the *Penicillium* spp. isolates described above; i.e. the isolates assigned Accession Nos. NRRL 21966, NRRL 21967, NRRL 21968, NRRL 21969 and NRRL 30489. The alternan is typically suspended at a level of about 0.5 to about 5%, and preferably at a level of 1-2%, in a liquid basal culture medium. An example of such a medium is "WW" described by Koenig et al. [Appl. Environ. Microbiol., (1989), 55:2079-2081] containing 2.5 g $KH_2PO_4$, 5.0 g $(NH_4)_2SO_4$, 0.1 g $CaCl_2$, 0.1 g $MgSO_4$ and 0.1 g NaCl per liter, pH 4.5. The medium is inoculated with spore suspensions of the *Penicillium* isolate. The culture medium is then incubated under conditions that favor germination of the spores. We have found that, by continuing the incubation for 4 days at 28° C., there is a noticeable shift from the native alternan having an apparent molecular weight of $2\text{-}10 \times 10^6$ to a modified alternan species having an apparent molecular weight of $5\text{-}10 \times 10^5$. After 17 days of incubation at 28° C., the predominant species of modified alternan has an apparent molecular weight of $1\text{-}5 \times 10^4$. The preferred modified alternans of the invention will have a molecular weight distribution between about $1 \times 10^4$ and $5 \times 10^5$, and more preferably between about $5 \times 10^4$ and $5 \times 10^5$. Within limits, the longer the cultivation is run, the more lower molecular weight species will be produced. For producing the preferred alternan species described above, the incubation period should be at least about 3 days at 28° C., and more preferably, at least about 7 days at 28° C. The temperature of incubation can also be varied, and will usually be selected to optimize spore germination and alternan modification as readily determined by a person in the art; though growth of the fungal organism on these media is limited. The cultivation temperature will typically be at least about 20° C., and preferably at least about 25° C. For the *Penicillium* spp. of the invention, 28° C. appears to be optimal.

Culture conditions for a given isolate can be determined by monitoring the levels of lower molecular weight alternan species in culture filtrates as the cultivation progresses. Reduction in optical density correlates with alternan molecular weight reduction and serves as a facile monitoring tool. A more sensitive characterization of molecular weight distribution can be conducted with high-performance size exclusion chromatography. Separations from the chromatography column are monitored with an optical rotation detector, and the optical rotation values and elution times can be compared to pollutant standards in order to estimate the molecular weight averages of modified alternans in the sample.

The mechanism of alternan modification by *Penicillium* spp. isolates is not clear. Culture supernatants, cell suspensions, and cell extracts are devoid of measurable alternanase enzyme activity. Furthermore, the pattern of progressive modification of alternan through seemingly discrete molecular weight species (discussed further, below) is unexpected.

The rheological properties, particularly viscosity and shear thinning, of the modified alternan produced in accordance with the invention resemble those of gum arabic and ultrasonicated alternan much more closely than the rheological properties of native alternan. It is, therefore, expected that the modified alternan would be useful as a functional replacement for gum arabic in applications requiring a low-viscosity, highly soluble bulking agent.

The relative viscosity of native alternan, modified alternan, ultrasonicated alternan and gum arabic were determined as a function of concentration (FIGS. 1-4). As shown by the shape of these curves, modified alternan is far more similar in rheological behavior to gum arabic and ultrasonicated alternan than to native alternan. Perhaps more significantly, the placement of each curve on the scale shows the native alternan is more viscous than the other three polysaccharides. Moreover, the function for native alternan shows an upward curve, indicating that the viscosity increases more or less exponentially with concentration, whereas the fungal-modified and sonicated alternan and the gum arabic show no such upward curve.

The lower viscosity of the modified alternan in comparison with the native form, allows for the preparation of solutions having a greater concentration of the polysaccharide. Solutions of native alternan greater than 12-15% w/v are difficult to attain; whereas modified alternan can be dissolved in water to give solutions of 50% w/v. This compares favorably with the levels of sonicated alternan (50% w/v) that can be put into solution and with the solubility of gum arabic (37% w/v) as reported in the Merck Index (1983).

The shear thinning behavior of native alternan, modified alternan, ultrasonicated alternan and gum arabic were determined at various concentrations (FIGS. 5-8). As shown by the flatness of these curves, all tested solutions are essentially Newtonian (and thus equivalent) with respect to shear thinning. Only at the highest tested concentrations, and very low shear rates, was any evidence of non-Newtonian behavior observed. Little pseudoplasticity was observed due to the relatively low viscosities encountered for these materials.

Modified alternan and gum arabic exhibited shear thinning only at concentrations several times higher than that of native alternan.

Figure 9:
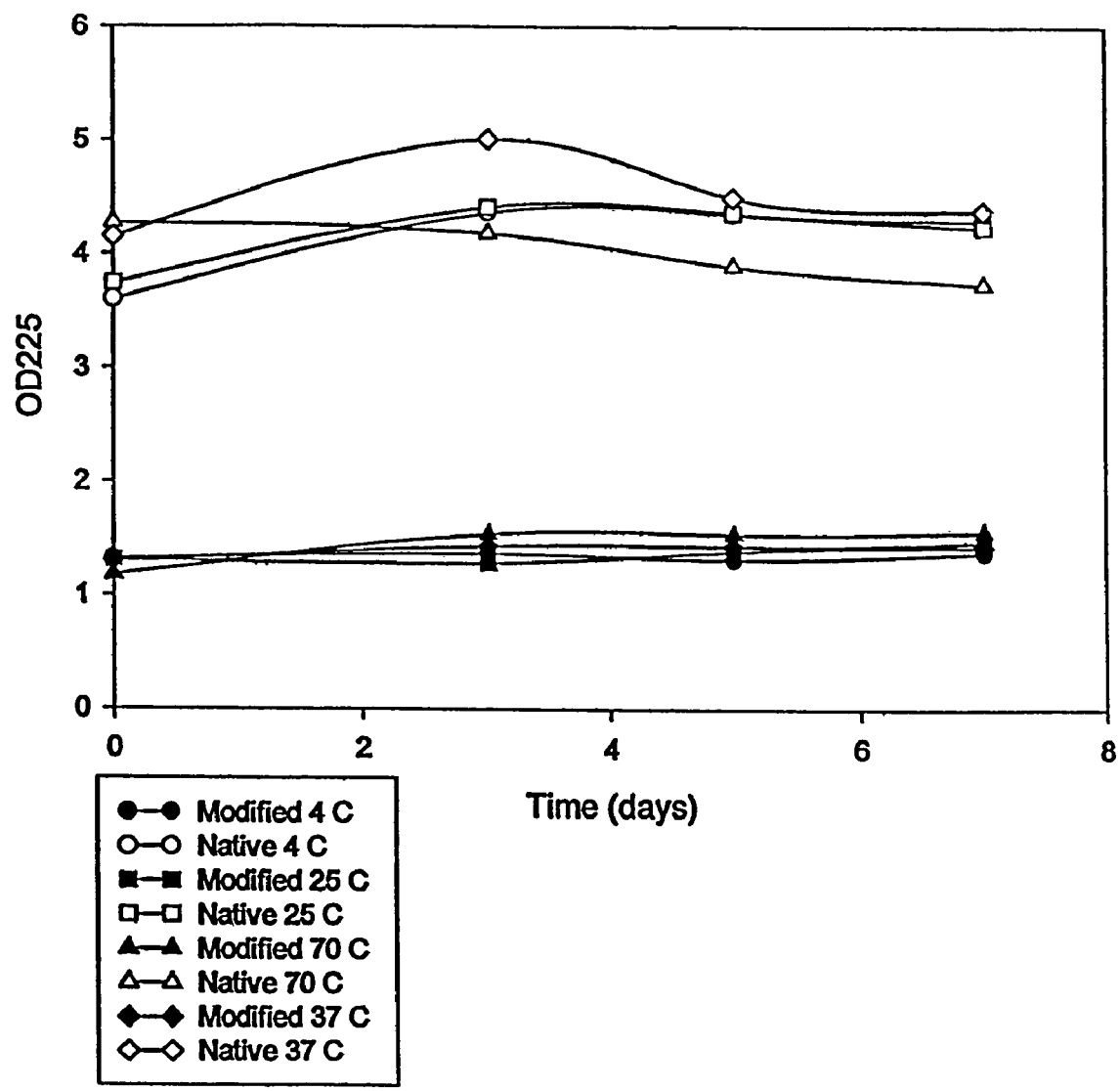
FIG. 9 is a plot illustrating the effect of temperature on alternan storage stability.
Figure 10:
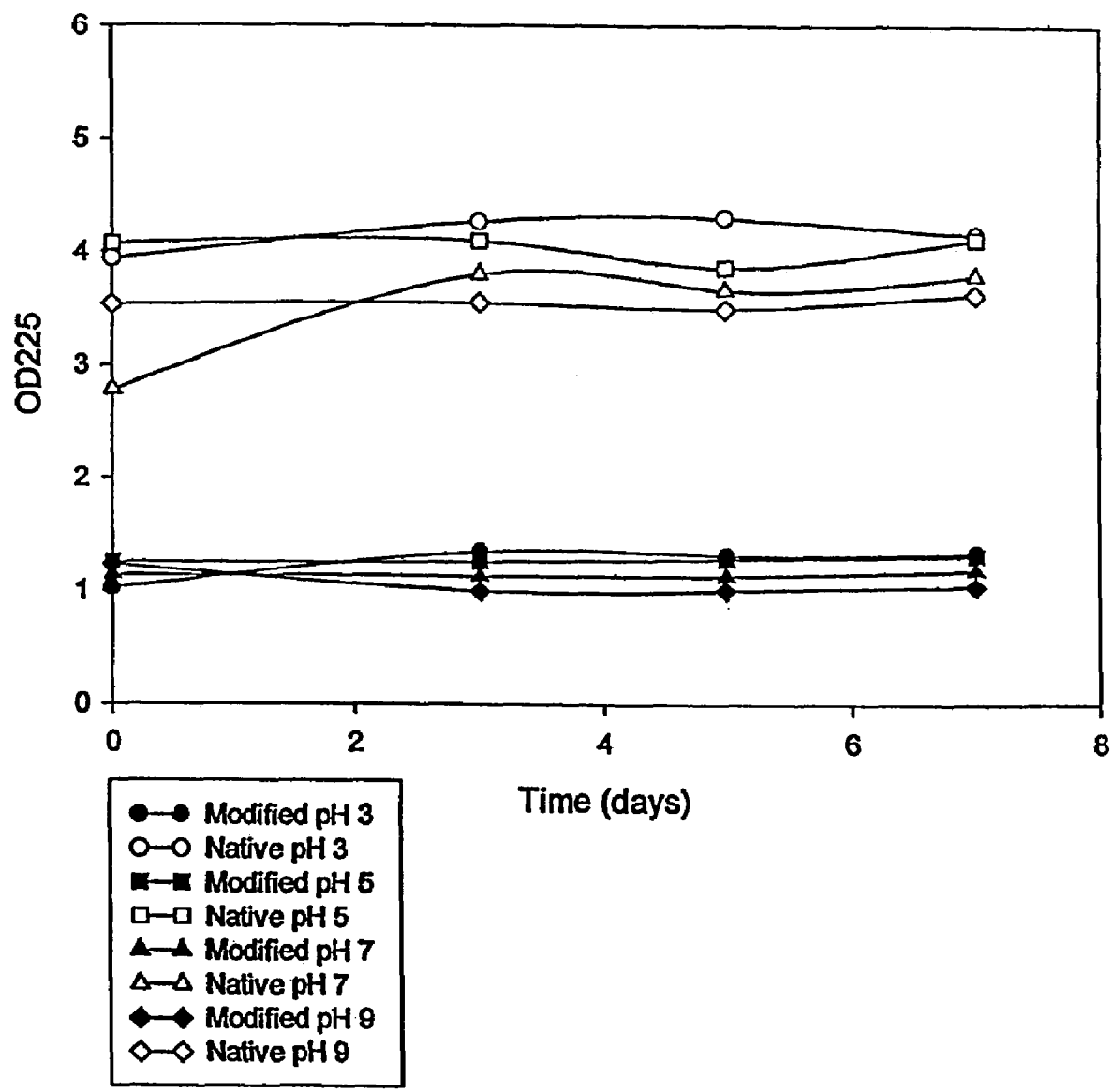
FIG. 10 is a plot illustrating the effect of pH on alternan storage stability.

End uses of the modified alternan of the invention will also be dictated in part by physical and functional properties other than the rheological and solubility properties described above. For example, methylation analysis reveals that the primary chemical structure of the modified alternan is virtually identical to those of both native alternan and sonicated alternan and different from that of gum arabic. Also, the modified alternan is similar to native alternan in not having any emulsification capacity. This is in contrast to gum arabic which has an emulsification capacity comparable to soy protein. As shown in FIGS. 9 and 10, the modified alternan is similar to the native form in terms of storage stability at various temperatures and pHs. One percent solutions of native alternan and modified alternan were made in defined medium (pH 5.0) and held for one week at temperatures between 4° C. and 70° C. The $OD_{225}$ of these solutions was monitored as a measure of alternan stability. As shown in FIG. 9, native alternan showed little fluctuation during this period, and modified alternan showed even less change. When solutions of native alternan and modified alternan were adjusted to various pH levels and stored for one week at 4° C., both native alternan and modified alternan exhibited excellent pH stability (FIG. 10). It is important to note that modified alternan showed no evidence of aggregation during storage. Both native alternan and modified alternan have storage advantages over gum arabic, which is readily contaminated by microbial growth (Glickman et al., 1959, Gum Arabic. In: Whistler R L, BeMiller J N (Eds) Industrial Gums: Polysaccharides and Their Derivatives, pp. 213-298, Academic Press, New York and London). Because of alternan's unique structure, microorganisms that grow on alternan are rare (Cote et al., 1992, Carbohydr. Polymers., 19:249-252). Similar to native alternan, the modified alternan is not highly hygroscopic, losing only 9-12% of its initial weight on desiccation and returning to within 0.3% of its initial weight when re-equilibrated. Also, both the native and modified alternans are bright white amorphous powders with no detectable flavor.

Figure 12:
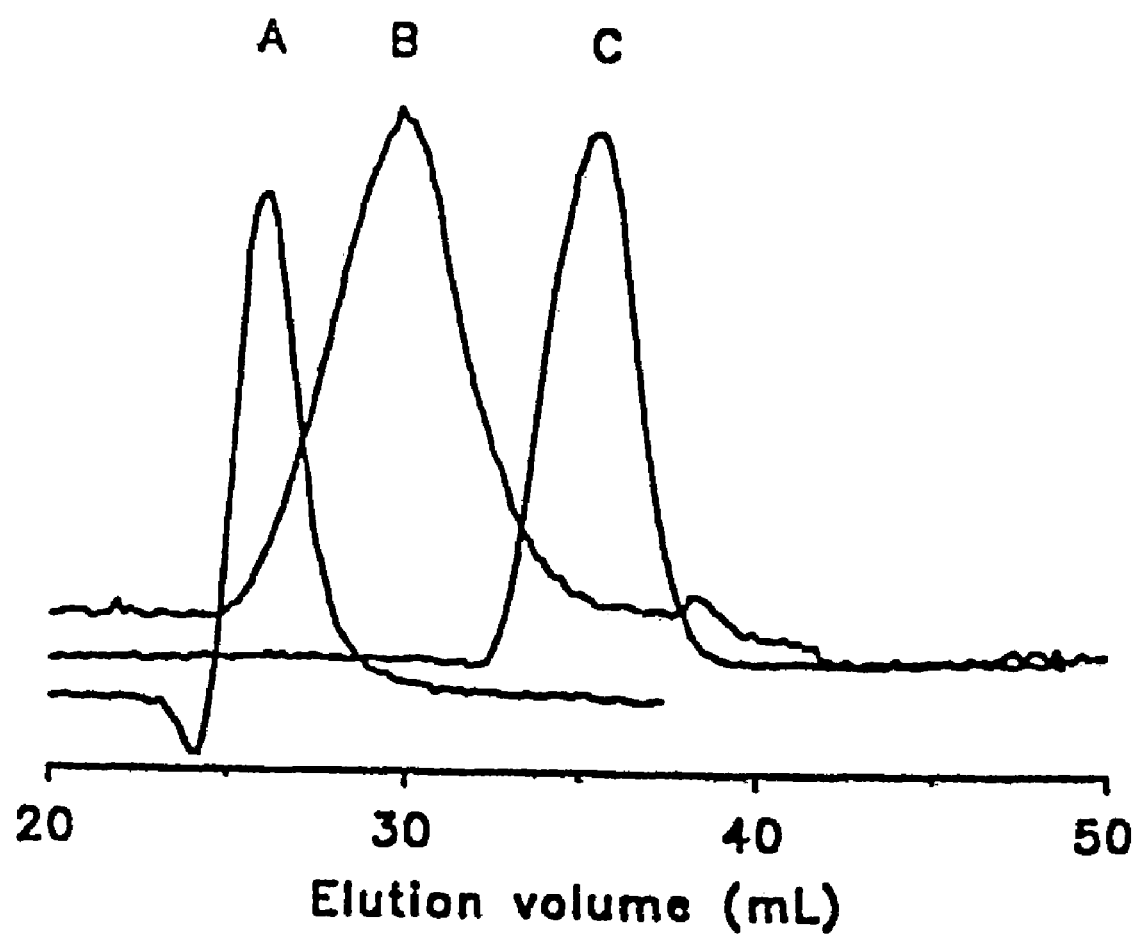
FIG. 12 illustrates high performance size exclusion chromatography (HPSEC) profiles of native, high-molecular-weight alternan (A), sonicated alternan (B), and isomaltodextanase-limit alternan (C).
Figure 13:
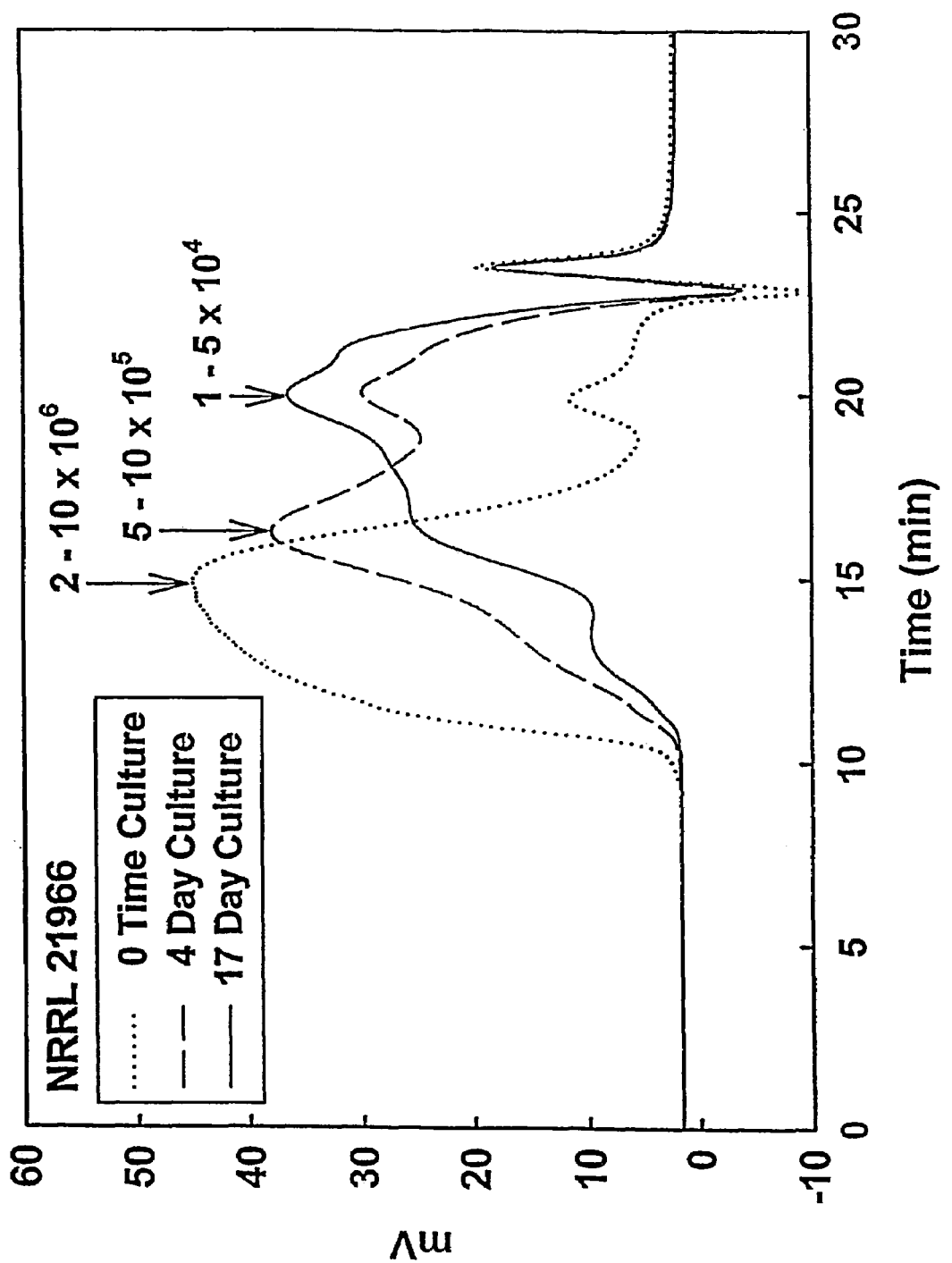
FIG. 13 is a characterization of strain NRRL 21966 alternan culture supernatants by HPSEC, wherein apparent molecular weight averages are indicated for major species present in culture samples.
Figure 14:
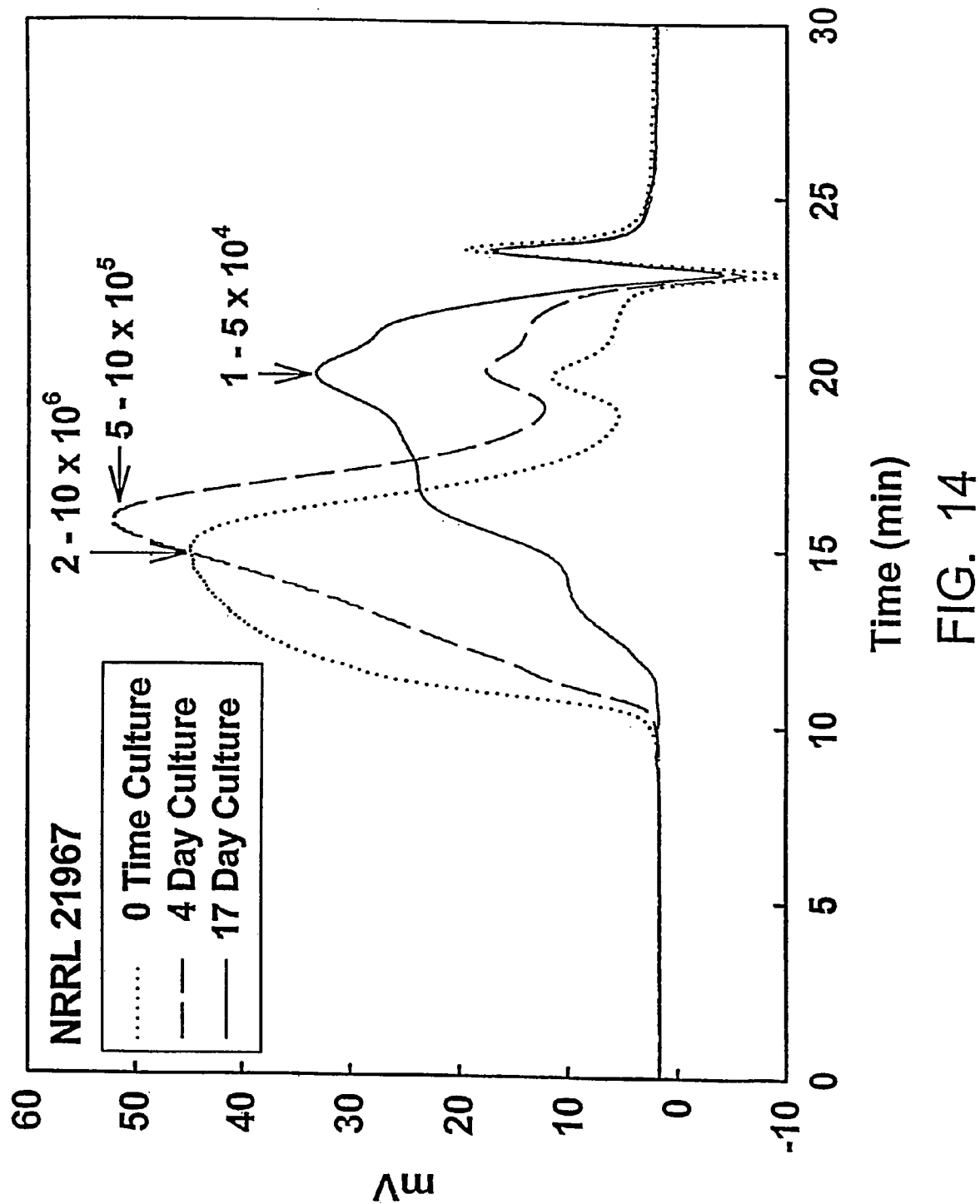
FIG. 14 is a characterization of strain NRRL 21967 alternan culture supernatants by HPSEC, wherein apparent molecular weight averages are indicated for major species present in culture samples.
Figure 15:
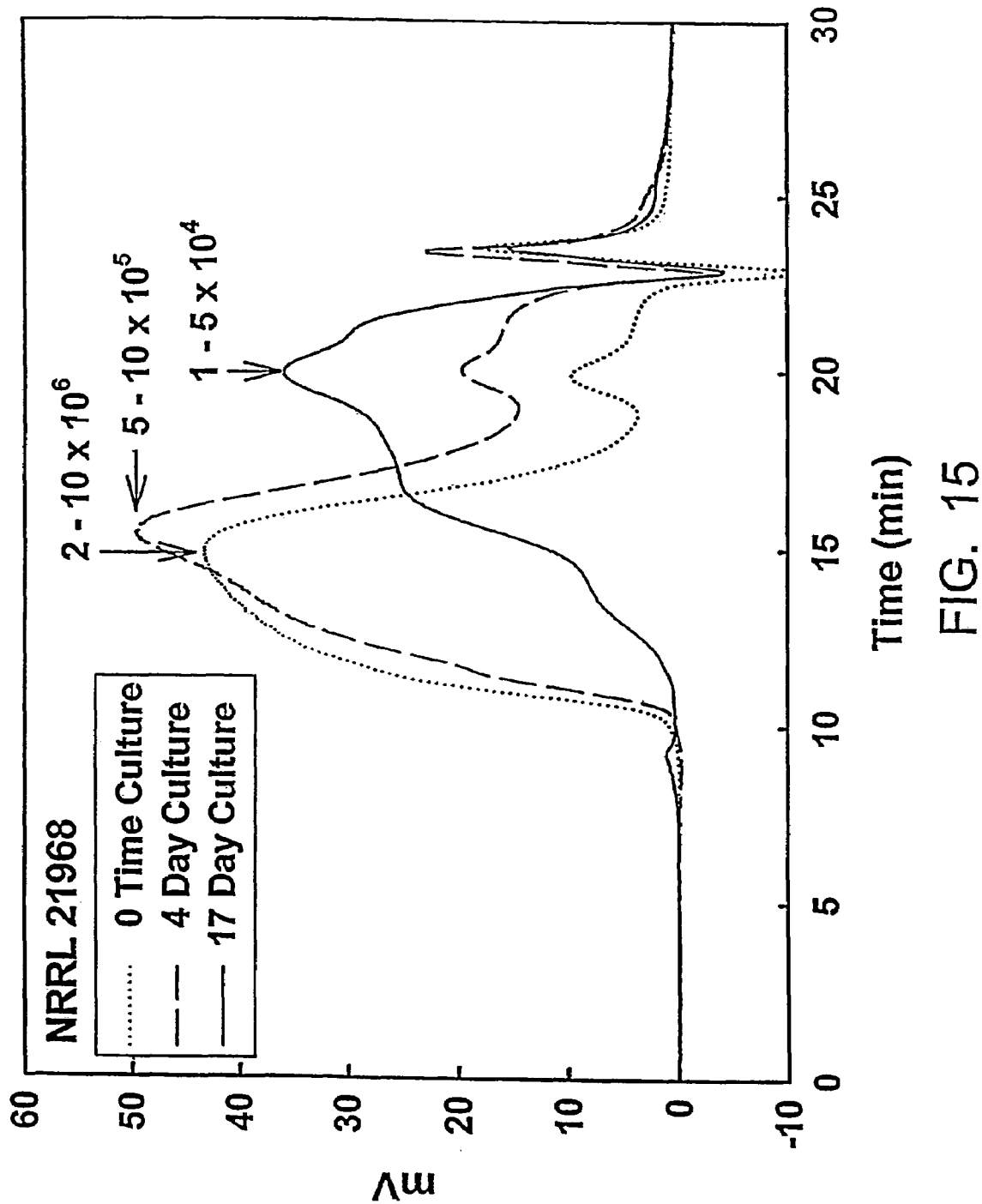
FIG. 15 is a characterization of strain NRRL 21968 alternan culture supernatants by HPSEC, wherein apparent molecular weight averages are indicated for major species present in culture samples.
Figure 16:
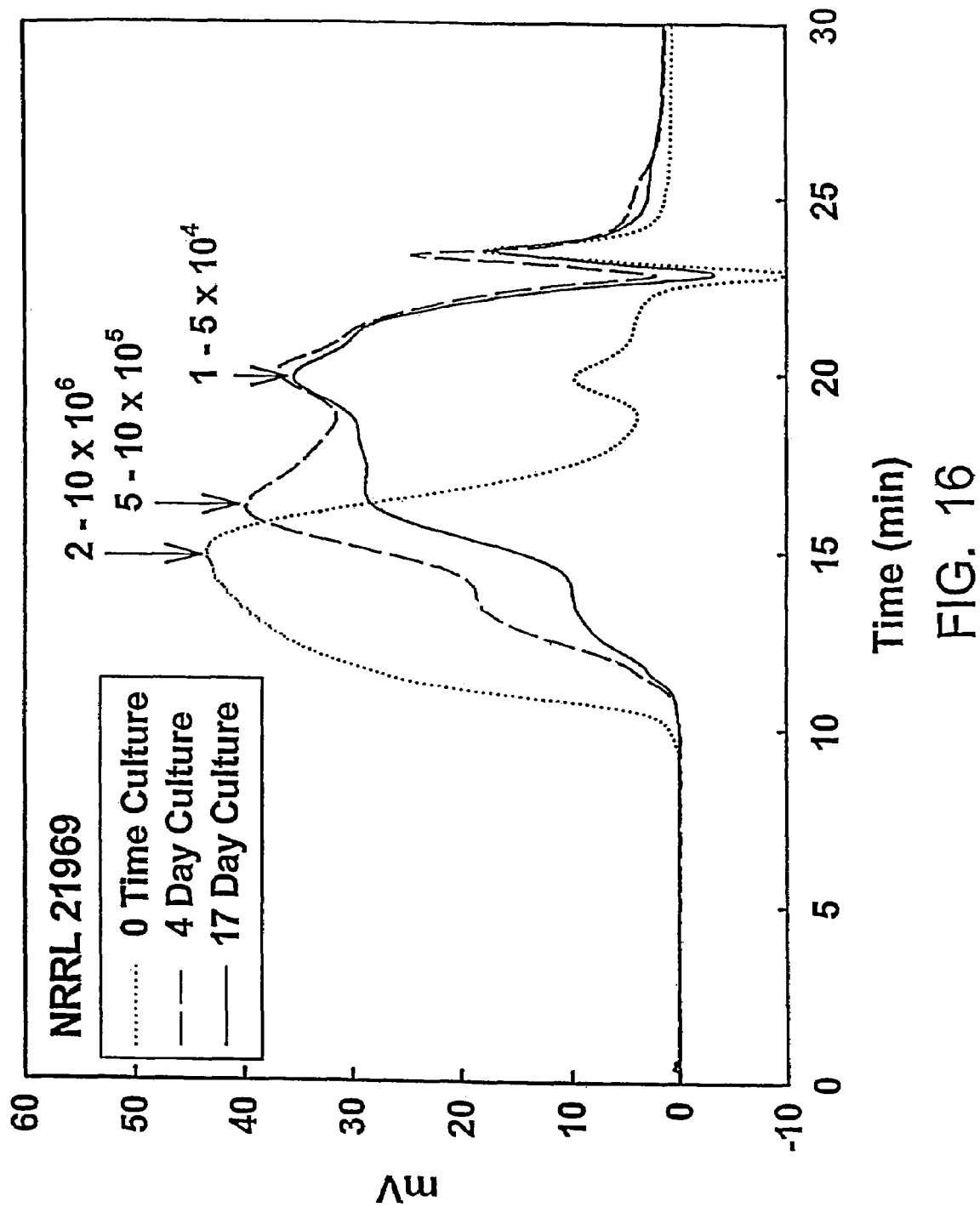
FIG. 16 is a characterization of strain NRRL 21969 alternan culture supernatants by high performance size exclusion chromatography, wherein apparent molecular weight averages are indicated for major species present in culture samples.

The significant physical difference between the modified alternan of the invention and other alternans as known in the art (including native alternan, limit alternan and sonicated alternan) relates to the molecular weight distribution. The prior art alternans are all monodisperse; that is, they each yield a single peak in HPLC (high performance liquid chromatography) analysis (FIG. 12). Though the breadth of the peak varies with the type of alternan, the molecular weights of the alternan species constituting that type revolve around a single value. In contrast, the subject modified alternans are heterodisperse; that is.they yield multiple, overlapping peaks in HPSEC analysis (FIGS. 13-16). This is indicative of the presence of discrete subpopulations of different molecular weights. The functional properties of the heterodisperse, modified alternan will expectedly be different from the monodisperse forms, giving rise to new end use applications for the modified alternan as a whole, or for any of the discrete subpopulations that could be isolated therefrom.

The following examples are intended to further illustrate the invention, without any intent for the invention to be limited to the specific embodiments described therein. All patents and publications cited herein are incorporated by reference.

EXAMPLE 1

Isolation of *Penicillium* spp. using Alternan Enrichment Cultures.

Soil samples from a Louisiana sugar cane field were serially diluted by a procedure similar to that of Will et al. [Biol. Fertil. Soils, 17:281-284, (1994), herein incorporated by reference]. Specifically, 2 grams of soil were diluted into 198 ml of sterile 0.2% agar in distilled water (water agar). This was shaken vigorously, and then 10 ml were transferred to 90 ml of water agar and mixed well. One ml of this suspension was then transferred into 9 ml of water containing 0.01% Triton-X 100. Aliquots (0.1 ml) of these final dilutions were used to inoculate 10 ml enrichment cultures, composed of 1.0% alternan in a basal medium that favored fungal growth ("WW," containing per liter 2.5 g $KH_2PO_4$, 5.0 g $(NH_4)_2SO_4$, 0.1 g $CaCl_2$ 0.1 g $MgSO_4$ and 0.1 g NaCl per liter, pH 4.5, described by Koenig et al. [Appl. Environ. Microbiol., 55:2079-2081 (1989)]), amended with 100 μg/ml chloramphenicol to further suppress bacterial growth. Enrichment cultures were incubated at 28° C. and 200 rpm for 7 days. The initial screening of enrichment cultures for alternan modification was performed by measuring the optical density of culture supernatants at 225 nm. Alternan solutions showed a maximal absorbance reading at 225 nm, and alternan concentrations were proportional to optical density at this wavelength. WW basal medium did not absorb strongly at 225 nm. Culture supernatants that showed a significant decrease in $OD_{225}$ after 7 days were diluted for single colony isolations on Potato Dextrose Agar (PDA, Difco, Detroit, Mich.). Isolates that retained their alternan modification phenotype were further purified by single spore isolation on Czapek's Agar (Difco, Detroit, Mich.).

Nearly half of approximately 40 enrichment cultures exhibited a reduction in the $OD_{225}$ of culture supernatants after 7 days of incubation, suggesting some degree of degradation or modification of alternan. The predominant organisms from these cultures were single-colony purified and retested in liquid medium containing alternan. Four isolates that consistently produced the greatest reductions in $OD_{225}$ were single-spore purified. These were identified as *Penicillium* spp. isolates, and deposited in the ARS Patent Culture Collection as strains NRRL 21966, NRRL 21967, NRRL 21968, and NRRL 21969. These isolates were derived from separate enrichment cultures, and differed slightly in colonial morphology, especially with respect to pigmentation. However, all four isolates have morphological characteristics consistent with *Penicillium subgenus Biverticillium*. None of the purified isolates exhibited clearing on dyed-alternan plates, suggesting that they were unable to degrade alternan to low molecular weight oligosaccharides that could easily diffuse in agar.

EXAMPLE 2

Maintenance and Growth of purified *Penicillium* spp.

*Penicillium* spp. isolates were routinely maintained on PDA slants, and stock spore suspensions were stored at −80° C. in 40% glycerol. Liquid cultures for alternan modification time course experiments contained the same medium used for enrichment cultures, with the omission of chloramphenicol. For each experiment, fresh spore suspensions were harvested from PDA plates, using sterile water containing 0.01% Triton-X100. Liquid cultures (10 ml in 50 ml flasks) were inoculated to $10^5$ spores/ml and incubated at 28° C. and 200 rpm for up to 17 days. For dry weight determinations, cultures were 100 ml in 500 ml flasks.

EXAMPLE 3

Comparison of *Penicillium* spp. Isolates For Ability to Modify Alternan.

Figure 11:
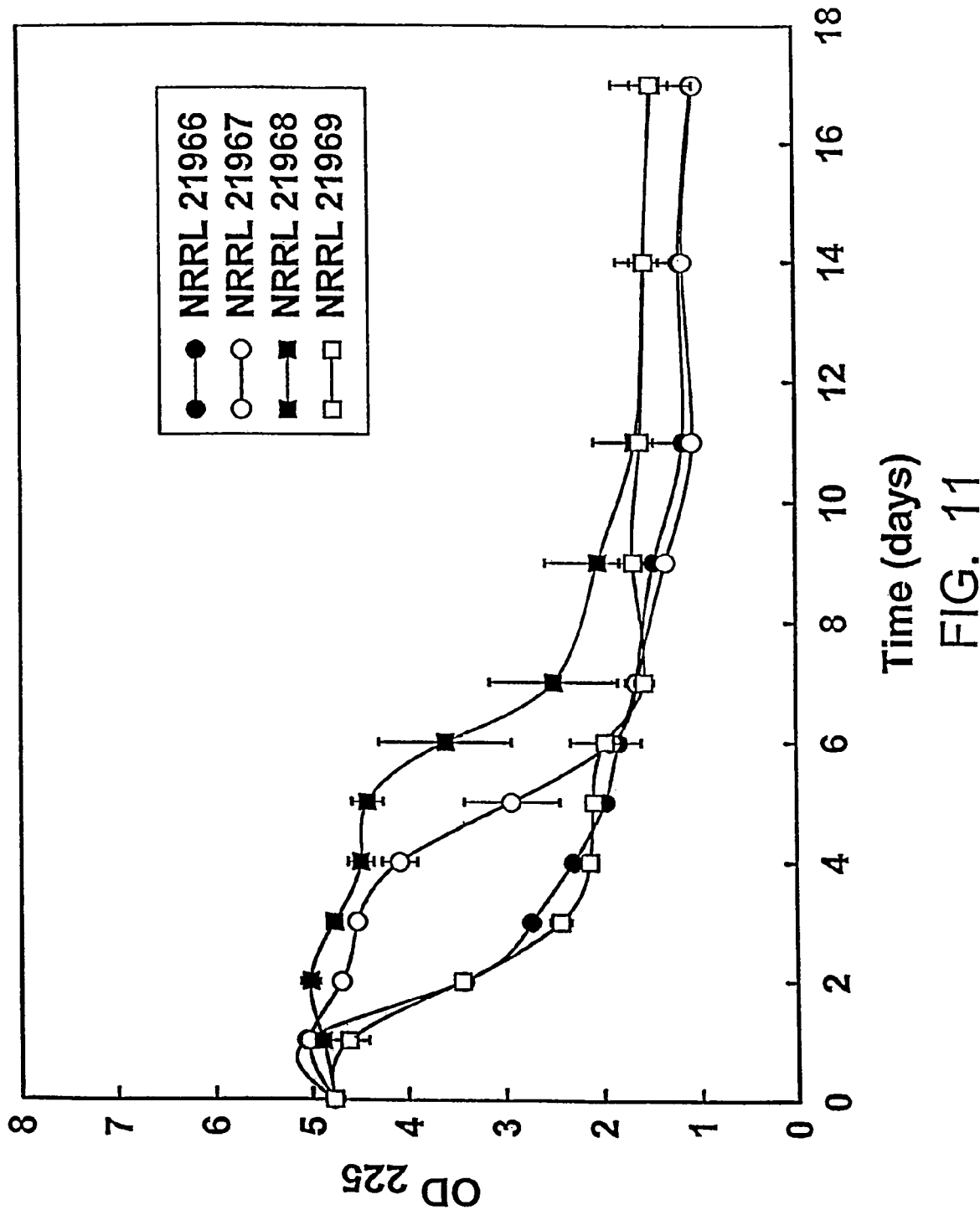
FIG. 11 is a plot showing. the effect of *Penicillium* spp. isolates on the $OD_{225}$ of alternan culture supernatants.

The four *Penicillium* spp. isolates were compared in parallel liquid alternan medium cultures as described in Example 2 over a 17 d time course (FIG. 11). As shown, strains NRRL 21966 and NRRL 21969 were similar in reducing the $OD_{225}$ of culture supernatants, effecting a change of approximately 3 OD units within 4 d. Strains NRRL 21967 and NRRL 21968 were somewhat slower in bringing about this change, although all cultures appeared similar by the end of the time course. By microscopic examination, spores of all four strains germinated synchronously and rapidly in alternan medium. However, the strains exhibited only limited growth on alternan, even after 17 d. In contrast, the strains appeared to grow well in cultures containing glucose in place of alternan. These differences were reflected in biomass dry weights measurements (Table 1). Phenol-sulfuric acid assays of alternan culture supernatants indicated no detectable change in total carbohydrate over 17 d. These results suggest that the *Penicillium* spp. isolates were largely unable to utilize alternan as a carbon source. However, since the spores failed to germinate in basal medium containing no carbon source, it is possible that the isolates utilized minor contaminants that may be present in alternan preparations, such as sucrose, maltose, dextrin, or protein.

EXAMPLE 4

Analysis of Modified Alternan.

One ml samples of fungal cultures were filtered through Nanosep MF 0.45 µm spin tubes (Pall Gelman Laboratory, Ann Arbor, MI.), and the filtrates were dried under vacuum (Speed Vac, Savant Instruments, Inc., Holbrook, N.Y.) and resuspended in 0.1 ml of distilled water. Samples (10 µl) were applied to a Shodex KB-806M high-performance size exclusion chromatography (HPSEC) column (Showa Denko K.K., Tokyo) and eluted with water at 0.5 ml/min. Separations were monitored using a Shodex OR-1 optical rotation detector (Showa Denko K.K.). Pullulan standards were used to estimate the molecular weight averages of unknowns (Showa Denko K.K.). Methylation analysis of modified alternan was performed by the method of Slodki et al. [Carbohyd. Res., 156:199-206, (1986)]. Total carbohydrate was estimated using the phenol-sulfuric acid method [Dubois et al., Analyt. Chem., 28:350-356 (1956)], using maltose as a standard. Alternanase activity was measured using a reducing sugar assay similar to that described by Biely et al. [Biely P. et al., Eur. J. Biochem., 226:633-639, (1994)].

Characterization of the molecular weight distribution of alternan from the culture supernatants by HPSEC is shown in FIGS. 13-16. Alternan present in the initial culture medium was predominantly represented by a high molecular weight peak of $2-10 \times 10^6$, consistent with previous characterizations of native alternan. These samples also contained a small amount of a lower molecular weight species of $1-5 \times 10^4$. For all isolates, samples from 4 d cultures exhibited a reduction in the high molecular weight native alternan species and the appearance of an intermediate molecular weight species of $5-10 \times 10^5$. Strains NRRL 21966 and NRRL 21969, which caused the most rapid reduction in $OD_{225}$, also showed a dramatic increase in the $1-5 \times 10^4$ species at day 4. At 17 d, samples from all four isolates featured the $1-5 \times 10^4$ peak as the predominant species, with an apparent shoulder corresponding to the intermediate molecular weight alternan species. Methylation analyses confirmed that the modified material in culture supernatants was alternan. Thus, the four fungal isolates appeared to differ one from another principally in the rate at which they progressively modified alternan towards lower molecular weight species.

The heterodisperse modified alternan of the invention contrasts with the monodisperse forms of alternan heretofore known in the art. This is illustrated by FIG. 12 which compares the HPSEC profiles for native, high-molecular-weight alternan (A), sonicated alternan (B), and isomaltodextranase-limit alternan (C).

EXAMPLE 5

Survey of Known *Penicillium subgenus Biverticillium* Cultures For Alternan Modification.

Ten isolates of *Penicillium subgenus Biverticillium*, (the same taxonomic group as the newly isolated alternan-modifying strains described above) representing 10 different species, were obtained from the Agricultural Research General Culture Collection (NRRL) in Peoria, Ill. Cultures were propagated on solid medium for spore production, and spores were harvested and tittered. Liquid cultures containing alternan were inoculated with equal numbers of spores ($10^5$/ml). Duplicate cultures were prepared for each isolate tested. Cultures were incubated for 7 days at 28° C. and 200 rpm, and optical densities of clarified culture supernatants were measured at 225 nm as a measure of alternan modification. One of the 10 tested isolates gave an $OD_{225}$ of 1.75±0.10 (as compared to 1.85±0.04 for control culture NRRL 2.1966), demonstrating a capacity to modify alternan. This isolate was deposited under the provisions of the Budapest Treaty in the Agricultural Research Patent Culture Collection (NRRL) in Peoria, IL., on Jul. 20, 2001, and has been assigned Accession No. NRRL 30489.

We claim:

1. A heterodisperse alternan comprising at least one species of modified lower molecular weight alternan relative to said native alternan, wherein said at least one species of modified lower molecular weight alternan has an average apparent molecular weight selected from the group of about $1-5 \times 10^4$ and about $5-10 \times 10^5$.

2. The heterodisperse alternan of claim 1, wherein said at least one species of modified lower molecular weight alternan has an average apparent molecular weight of about $1-5 \times 10^4$.

3. The heterodisperse alternan of claim 1, wherein said at least one species of modified lower molecular weight alternan has an average apparent molecular weight of about $5-10 \times 10^5$.

4. The heterodisperse alternan of claim 1, wherein a first species of said at least one species of modified lower molecular weight alternan has an average apparent molecular weight of about $1-5 \times 10^4$ and a second species of said at least one species of modified lower molecular weight alternan has an average apparent molecular weight of about $5-10 \times 10^5$.

* * * * *